US009469677B2

(12) United States Patent
Beniash et al.

(10) Patent No.: US 9,469,677 B2
(45) Date of Patent: *Oct. 18, 2016

(54) BIOMIMETIC COATING OF MAGNESIUM ALLOY FOR ENHANCED CORROSION RESISTANCE AND CALCIUM PHOSPHATE DEPOSITION

(71) Applicant: UNIVERSITY OF PITTSBURGH—OF THE COMMONWEALTH SYSTEM OF HIGHER EDUCATION, Pittsburgh, PA (US)

(72) Inventors: Elia Beniash, Mt. Lebanon, PA (US); Charles S. Sfeir, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 27 days.

This patent is subject to a terminal disclaimer.

(21) Appl. No.: 14/540,575

(22) Filed: Nov. 13, 2014

(65) Prior Publication Data

US 2015/0132356 A1 May 14, 2015

Related U.S. Application Data

(63) Continuation-in-part of application No. 14/079,086, filed on Nov. 13, 2013, now Pat. No. 9,221,888.

(60) Provisional application No. 61/903,741, filed on Nov. 13, 2013.

(51) Int. Cl.
| A61K 38/10 | (2006.01) |
| A61K 38/16 | (2006.01) |
| C01F 5/00 | (2006.01) |
| A61L 27/28 | (2006.01) |

(Continued)

(52) U.S. Cl.
CPC .............. *C07K 14/47* (2013.01); *A61L 31/022* (2013.01); *A61L 31/047* (2013.01); *A61L 31/10* (2013.01); *A61L 31/16* (2013.01); *A61L 2300/25* (2013.01); *A61L 2300/252* (2013.01); *A61L 2300/606* (2013.01); *A61L 2430/02* (2013.01)

(58) Field of Classification Search
None
See application file for complete search history.

(56) References Cited

U.S. PATENT DOCUMENTS

| 7,846,445 B2 | 12/2010 | Schellenberger et al. |
| 7,855,279 B2 | 12/2010 | Schellenberger et al. |

(Continued)

OTHER PUBLICATIONS

George, et al.; "The Carboxyl-Terminal Domain of Phosphophoryn Contains Unique Extended Triplet Amino Acid Repeat Sequences Forming Ordered Carboxyl-Phosphate Interaction Ridges That May Be Essential in the Biomineralization Process"; The Journal of Biological Chemistry; Dec. 20, 1996; pp. 32869-32873; vol. 271 No. 51.

(Continued)

*Primary Examiner* — Elizabeth C Kemmerer
(74) *Attorney, Agent, or Firm* — Eckert Seamans Cherin & Mellott, LLC; Carol A. Marmo

(57) ABSTRACT

The invention relates to biomimetic peptide-containing compositions for use, in particular, for application and or deposition on a magnesium alloy, e.g., substrate, to at least partially coat a surface of the magnesium alloy. The invention also relates to the coated magnesium alloy which is particularly useful for tissue and bone repair and regeneration applications, such as, for constructing medical implant devices.

8 Claims, 2 Drawing Sheets

(51) Int. Cl.
    *A61L 27/04*     (2006.01)
    *C07K 14/47*     (2006.01)
    *A61L 31/02*     (2006.01)
    *A61L 31/04*     (2006.01)
    *A61L 31/10*     (2006.01)
    *A61L 31/16*     (2006.01)

(56) References Cited

U.S. PATENT DOCUMENTS

| | | | |
|---|---|---|---|
| 8,492,530 | B2 | 7/2013 | Schellenberger et al. |
| 9,221,888 | B2 * | 12/2015 | Beniash et al. |
| 2007/0087959 | A1 | 4/2007 | Sfeir et al. |
| 2008/0039341 | A1 | 2/2008 | Schellenberger et al. |
| 2009/0098050 | A1 | 4/2009 | Yarbrough et al. |
| 2011/0218585 | A1 * | 9/2011 | Krinke et al. .............. 606/86 R |
| 2013/0060348 | A1 * | 3/2013 | Hodgkinson et al. ..... 623/23.75 |

OTHER PUBLICATIONS

Ritchie, et al.; A Novel Rat 523 Amino Acid Phosphophoryn: Nucleotide Sequence and Genomic Organization; Biochimica et Biophysica Acta, 1520; Jul. 9, 2001; pp. 212-222.

Deshpande, et al.; "Primary Structure and Phosphorylation of Dentin Matrix Protein 1 (DMP1) and Dentin Phosphophoryn (DPP) Uniquely Determine Their Role in Biomineralization" Bio Macromolecules; Jul. 8, 2011; pp. 2933-2945.

Cui, et al.; "Biomimetic Coating of Magnesium Alloy for Enhanced Corrosion Resistance and Calcium Phosphate Deposition"; Acta Biomaterialia; Jun. 29, 2013; pp. 8650-8659.

Sfeir, et al.; "Synthesis of Bone-Like Nanocomposites Using Multiphosphorylated Peptides"; Acta Biomaterialia; Jan. 13, 2014; pp. 2241-2249.

* cited by examiner

BIOMIMETIC COATING OF MAGNESIUM ALLOY FOR ENHANCED CORROSION RESISTANCE AND CALCIUM PHOSPHATE DEPOSITION

CROSS-REFERENCE TO RELATED APPLICATIONS

This application is a Continuation-In-Part (CIP) of U.S. non-provisional patent application Ser. No. 14/079,086, entitled "Bone Substitute Nanocomposites and Methods of Synthesis Using Multiphosphorylated Peptides" filed on Nov. 13, 2013, and issued as U.S. Pat. No. 9,221,888 B2 on Dec. 29, 2015, which claims priority under 35 U.S.C. §119(e) from U.S. provisional patent application No. 61/725,796, entitled "Bone Substitute Nanocomposites and Methods of Synthesis Using Multiphosphorylated Peptides" and filed on Nov. 13, 2012, and this application claims priority under 35 U.S.C. §119(e) from U.S. provisional patent application No. 61/903,741, entitled "Biomimetic Coating of Magnesium Alloy for Enhanced Corrosion Resistance and Calcium Phosphate Deposition" and filed on Nov. 13, 2013, the contents of which are all incorporated herein by reference.

BACKGROUND OF THE INVENTION

1. Field of the Invention

This invention relates generally to coating compositions and coated substrates. In particular, the invention includes biomimetic peptide-containing coating compositions and magnesium alloy substrates having applied thereto, or deposited thereon, the biomimetic peptide-containing compositions, wherein the coated magnesium alloy substrates are useful for tissue and bone repair and regeneration, such as but not limited to, as medical implant devices in orthopedic, craniofacial, dental and cardiovascular surgeries.

2. Background Information

Biomedical implant devices are known in the art and are commonly used in the practice of various surgeries, such as, orthopedic, dental, craniofacial and cardiovascular implant surgeries. These devices may be used for various purposes, such as but not limited to, tissue and bone regeneration, and drug or biomolecule delivery. Furthermore, stents are also implanted into a body of a patient to support lumens, for example, coronary arteries. Implant devices include, but are not limited to, scaffolds, such as plates and screws. Biomaterials for the construction of implant devices are typically chosen based on their ability to withstand cyclic load-bearing and compatibility with the physiological environment of a human body. Many of these implant devices are traditionally constructed of polymer or metal. These materials of construction exhibit good biomechanical properties. Metallic biomaterials, in particular, have appropriate properties such as high strength, ductility, fracture toughness, hardness, corrosion resistance, formability, and biocompatibility to make them attractive for most load bearing applications. Polymers, such as polyhydroxy acids, polylactic acid (PLA), polyglycolic acid (PGA), and the like, are known as conventional biomaterials, however, in some instances the strength and ductility exhibited by polymers is not as attractive as that demonstrated by metallic biomaterials. For example, it is known to use stainless steel or titanium biomedical implants for clinical applications which require load-bearing capacities.

Metallic and polymer biomaterials are not biodegradable and therefore, other biomaterials need to be used wherein there is an interest to provide a biodegradable implant device such that the device is capable of degrading over a period of time, e.g., by dissolving in the physiological environment, and surgery is not required for remove when there is no longer a medical need for the implant device. Magnesium is potentially attractive as a biomaterial because it is very lightweight, has a density similar to cortical bone, has an elastic modulus close to natural bone, is essential to human metabolism, is a cofactor for many enzymes, and stabilizes the structures of DNA and RNA. Magnesium-based implants may be degradable in-vivo through simple corrosion and exhibit mechanical properties similar to native bone.

There are, however, disadvantages associated with magnesium which have restricted its use in medical applications. For example, magnesium is very reactive in nature and is susceptible to rapid corrosion as opposed to gradual degradation, particularly, in high chloride environments such as those created by human body fluids and blood plasma, and in aqueous solutions having a pH of 11 or less. The physiological pH is typically in the range of 7.4 to 7.6. During magnesium corrosion, a local pH increase as well as hydrogen liberation may ensue. If the evolution of gas is too rapid, it cannot be absorbed by the body and poses a significant concern for medical applications.

In order for magnesium to be considered an acceptable biomaterial for tissue and bone replacement and regeneration, improvement of its corrosion resistance is needed. Thus, there have been methods developed in the art for the purpose of improving the corrosion resistance of magnesium. Known methods include element alloying and surface modification or coating.

Traditional surface modification methods include electrochemical plating, chemical conversion, anodizing, gas phase deposition, and organic coatings. An effective and mature chemical conversion process known in the art is based on using a chromate bath. However, use the chromate bath is limited due to its high toxicity. The application of plating and anodizing techniques are also limited by their dependence on toxic heavy metal ions and their adverse effects on fatigue properties.

Known magnesium alloy coatings typically include the use of ceramic, chitosan, and various forms of calcium phosphate (CaP). Application of a CaP coating by ion-beam-assisted deposition or various types of electrochemical and chemical treatments can provide a reduced corrosion rate. However, the crystal structure, chemical composition, coating morphology, and the measured degradation rates can exhibit variability. In addition, even though initially good cell adhesion and spreading of CaP coatings has been demonstrated, cell viability has shown to be compromised at longer time periods, which is likely due to the poor corrosion protection of CaP alone.

Other known coatings have also demonstrated variable results in enhancing corrosion resistance or a lack bioactive properties necessary for controlling cellular behavior. Further, coupling of the coatings to magnesium-based alloys as well as non-resorbable metals, such as titanium, have generally produced low coating affinity/low bonding strength on the alloy itself.

Further, in considering biologically-derived surface coatings or modifiers, such as peptides, for use in coating magnesium alloy, it is known that bone and dentin are examples of mineralized tissue, which are unique, hierarchical nanocomposites and can include about 70% by weight carbonated apatite, 20-25% by weight organic matrix, and 5-10/% by weight water. Mineralized collagen fibrils are the major organic components, e.g., building blocks, of these tissues. Other non-collagenous proteins (NCPs) and glycoproteins account for less than about 10% of the total organic content and contribute to the regulation of mineralization, cell signaling and mechanical performance of the tissue. It has been shown that the mineral component in mineralized collagen fibrils has almost two times greater strain than geologic or synthetic apatite, and the organic component is significantly stiffer than non-mineralized collagen. Furthermore, the interlaced structure of the mineralized collagen fibrils provide a complex organization and unique mechanical properties.

NCPs are involved in collagen mineralization and a characteristic of NCPs is the disproportionately large percentage of acidic amino acids such as Asp, Glu and Ser$^{(P)}$. For example, the major NCP in dentin is phosphophoryn (DPP). DPP includes primarily Ser-Ser-Asp repeat motifs with more than 90% of serines phosphorylated.

Protein phosphorylation is one of the most common post-translational modifications. However, the vast majority of phosphorylated proteins contain only a small amount of phosphorylation sites adjacent to kinase-specific recognition motifs. The precise phosphorylation mechanisms of the highly phosphorylated proteins from the mineralized tissues are not completely understood in the art. It has been proposed that casein kinases (CK) 1 and 2 phosphorylate DPP intracellularly in the endoplasmic reticulum. According to certain hypotheses, phosphorylation occurs via a chain or hierarchical reaction wherein one phosphorylated serine becomes a part of the CK recognition site which leads to subsequent phosphorylation of new serines. CK transfer γ-phosphate of ATP (or GTP) to the hydroxyl group of serine or threonine, or to the phenolic hydroxyl on tyrosine residues in proteins.

A number of peptides mimicking NCPs have been synthesized. However, the known syntheses for preparing bio-inspired peptides has limitations. For example, introducing any single phosphorylated amino-acids during peptide synthesis leads to a significant decrease in yield, thereby limiting the total number of phosphorylated amino acids that can be added to a peptide.

Thus, there is a need in the art for magnesium alloy-containing composites for tissue and bone replacement and regeneration, such as tissue and bone implants, which exhibit the non-toxicity and mechanical properties that are desired while demonstrating reduced rate of corrosion when exposed to physiological conditions. It is an objective of this invention to design and develop novel biomimetic peptide-containing compositions for application to or deposition on magnesium alloy such as to form a coating on a surface of the magnesium alloy. It is desirable for these biologically-derived coatings and coated magnesium alloys to be effective for magnesium corrosion control, calcium phosphate (CaP) deposition, and cell signaling capabilities to enhance tissue regeneration.

SUMMARY OF THE INVENTION

In one aspect, the invention provides a composition for coating magnesium alloy. The composition includes a peptide selected from the group consisting of: DEDE(SSD)$_n$DEG, wherein n is an integer from 2 to 20, indicated by SEQ NO. 1; RRRDEDE(SSD)$_n$DEG, wherein n is an integer from 2 to 20, indicated by SEQ NO. 2; RRRGDEDE(SSD)$_n$DEG, wherein n is an integer from 2 to 20, indicated by SEQ NO.3; and LKKLKKLDEDE(SSD)$_n$DEG, wherein n is an integer from 2 to 20, indicated by SEQ NO. 4.

In certain embodiments, the peptide is selected from the group consisting of DEDESSDSSDSSDDEG, indicated by SEQ NO. 1; RRRDEDESSDSSDSSDDEG, indicated by SEQ NO. 2; RRRDEDESSDSSDSSDSSDDEG, indicated by SEQ NO. 2; and RRRGDEDESSDSSDSSDDEG, indicated by SEQ NO. 3.

In another aspect, the invention provides a coated magnesium alloy substrate, which includes a coating composition, which includes a peptide selected from the group consisting of: DEDE(SSD)$_n$DEG, wherein n is an integer from 2 to 20, indicated by SEQ NO. 1; RRRDEDE(SSD)$_n$DEG, wherein n is an integer from 2 to 20, indicated by SEQ NO. 2; RRRGDEDE(SSD)$_n$DEG, wherein n is an integer from 2 to 20, indicated by SEQ NO.3; and LKKLKKLDEDE(SSD)$_n$DEG, wherein n is an integer from 2 to 20, indicated by SEQ NO. 4.

In certain embodiments, the peptide is selected from the group consisting of DEDESSDSSDSSDDEG, indicated by SEQ NO. 1; RRRDEDESSDSSDSSDDEG, indicated by SEQ NO. 2; RRRDEDESSDSSDSSDSSDDEG, indicated by SEQ NO. 2; and RRRGDEDESSDSSDSSDDEG, indicated by SEQ NO. 3.

In yet another aspect, the invention provides a method of preparing a biomimetic magnesium alloy medical device. The method includes making a coating composition including 3DSS peptide; depositing the coating composition on a least a portion of an outer surface of an uncoated magnesium alloy medical device to form a coating thereon; and producing a coated magnesium alloy medical device.

In certain embodiments, the forming and the depositing of the coating composition, includes dissolving 3DSS powder in an organic solvent to form a 3DSS solution; combining the 3DSS solution with CaP solution to form a 3DSS/CaP bath solution; immersing the uncoated magnesium alloy medical device into the 3DSS/CaP bath solution to form the coating on the surface of the magnesium medical device.

THE SEQUENCE LISTING

Figure 1:
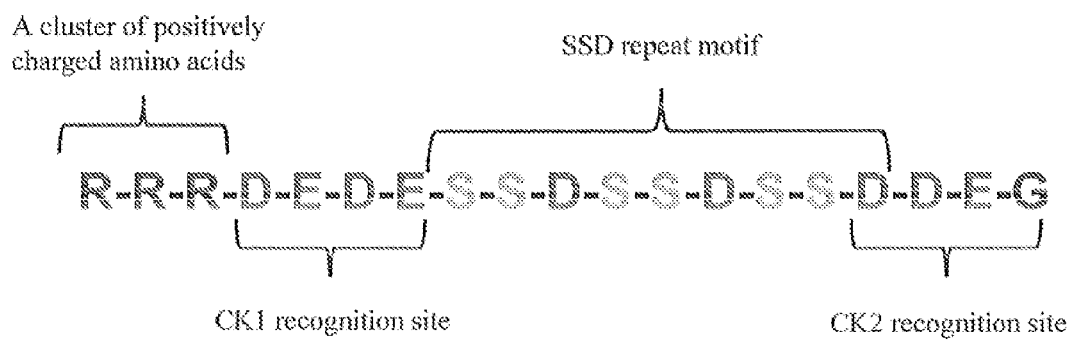
FIG. 1 is a peptide design schematic which shows a R-SSD3 sequence containing: i) three Arg amino acids at its N-terminus end, ii) followed by four amino acids forming the CK1 recognition site and iii) three Ser-Ser-Asp repeats. CK2 recognition motif is located at the C-terminus end of the peptide. This peptide design schematic is in accordance with certain embodiments of the invention and is indicated by SEQ NO. 2.

The amino acid sequences listed in the accompanying sequence listing are shown using standard letter abbreviations and the sequence listing is incorporated by reference herein.

DETAILED DESCRIPTION OF THE INVENTION

The invention relates to novel biomimetic peptide-containing compositions, metal alloys having applied thereto or deposited thereon the biomimetic peptide-containing compositions and, coated metal alloy substrates and articles for use in tissue and bone repair and regeneration, such as but not limited to, medical implant devices in orthopedic, craniofacial, dental and cardiovascular surgeries.

The coated magnesium alloys in accordance with the invention include at least one of the following properties: biocompatibility, corrosion resistance, biodegradability, cell attachment, cell viability and mechanical strength, which make them suitable for use as implant devices in a body of a patient.

The magnesium alloys for use in the invention include magnesium and at least one different elemental metal. The at least one different elemental metal can be selected from a wide variety of elemental metals that are known in the art. In certain embodiments, the at least one different metal can be selected from iron, zirconium, manganese, calcium, yttrium and zinc. The amount of each of the components in the magnesium alloy composition can vary and in general, the amounts are selected such that the resulting composition is within acceptable non-toxic limits, sufficiently biocompatible and degradable over a period of time. For example, the components and their amounts may be selected such that the magnesium alloy composition exhibits corrosion resistance in the presence of water and body fluids, which allows for suitable in vitro use in a physiological environment, e.g., patient body, and exhibits corrosion resistance with minimal or no evolution of hydrogen gas as the evolution of hydrogen, e.g., hydrogen bubbles, may cause complications in a patient body.

Further, in accordance with certain embodiments of the invention, the biomimetic peptide-containing coating is effective to reduce the corrosion rate of the magnesium alloy when subjected to body fluids and furthermore, is effective to reduce or preclude the evolution of hydrogen gas from the magnesium alloy.

It is contemplated that other components may be added to the magnesium alloy provided that the non-toxicity, biocompatibility and degradability remain within acceptable limits. Acceptable non-toxic limits and time frames for degradation can vary and can depend on the particular physical and physiological characteristics of the patient, in vitro site of implantation and medical use of the device. Non-limiting examples of suitable other components include aluminum, silver, cerium and/or strontium.

In certain embodiments of the invention, the magnesium alloy is composed of magnesium, zinc and aluminum. The amount of each component can vary and in certain embodiments each is present in the following weight percent based on total weight of the magnesium alloy composition: about 96% magnesium, about 1% zinc and about 3% aluminum.

In certain embodiments, the magnesium alloy is formed by subjecting the metal element components to high energy mechanical alloying (HEMA) and uniaxial or isostatic compaction and sintering.

Non-limiting examples of magnesium alloys include those described in PCT Application having International Application No. PCT/US2012/058939 entitled "Biodegradable Metal Alloys" filed on Oct. 5, 2012 and based on United States Provisional Patent Application 61/544,127 entitled "Biodegradable Metal Alloys" filed on Oct. 6, 2011; and U.S. Provisional Patent Application 61/710,338 entitled "Biodegradable Iron-Containing Compositions, Methods of Preparing and Applications Therefor" filed on Oct. 5, 2012, which are incorporated in their entirety herein by reference.

The magnesium alloys can be used to form or fabricate a substrate. In certain embodiments, the substrate is a medical device, such as, a medical implant device. Non-limiting examples of medical implant devices include scaffolds, such as but not limited to, plates, meshes, staples, screws, pins, tacks, rods, suture anchors, tubular mesh, coils, x-ray markers, catheters, endoprostheses, pipes, shields, bolts, clips or plugs, dental implants or devices, graft devices, bone-fracture healing devices, bone replacement devices, joint replacement devices, tissue regeneration devices, cardiovascular stents, nerve guides, surgical implants and wires.

In accordance with the invention, a peptide-containing composition is applied to, or deposited on, the magnesium alloy to at least partially form a layer or thin film or coating on a surface of the magnesium alloy. Methods for application or deposition of the coating composition can be selected from various conventional coating techniques known in the art and traditional apparatus used therefor. Non-limiting examples include, but are not limited to spraying, brushing, wiping, dipping, immersing in a bath, and the like. Furthermore, the thickness of the layer, thin film or coating can vary and may depend on the method of application, the components of the composition and the desired properties of the coated substrate or article.

Some conventional coating methods may not be effective to produce non-uniform and porous coatings on magnesium alloy substrates. Technical difficulties typically arise from hydrogen bubbles formed on the magnesium alloy surface during the coating process. Some known coating methods for magnesium alloy surface modification involve immersion of magnesium alloy substrates into an aqueous environment. Immersion often includes the interference of corrosion effects on the coating formation, resulting in low coating affinity and/or low bonding strength on the actual magnesium alloy surface. Thus, a non-aqueous environment can be employed for magnesium alloy substrates using an organic solution (e.g., tetrahydrofuran (THF)) as a solvent for the biomimetic peptide coating. This method provides an advantage of conserving the surface integrity while forming a homogeneous coating on the magnesium alloy without concomitant corrosion reaction. It is also likely that increasing the amount of peptide may result in a thicker coating on the magnesium alloy surface and therefore better corrosion resistance. However, enhanced performance is typically balanced against increased cost.

Generally, calcium (in the mineral phase of bone and dentin), is naturally biocompatible, non-toxic and therefore, a material of interest in orthopaedic applications. Various phases of calcium phosphate (CaP) have been explored in the art for coating medical devices, including hydroxyapatite (HA), octacalcium phosphate (OCP), calcium phosphate dehydrate (DCP), anhydrous calcium phosphate (ADCP), and tricalcium phosphate (TCP). For example, it is known in the art to apply CaP coatings to magnesium alloys and, there are various conventional apparatus and methods known for application of the CaP coatings. Conventional methods include immersing the substrates into various types of simulated body fluids (SBF) at different temperatures. It is well established in the art that chloride ion ($Cl^-$) can promote corrosion by rapidly destroying the magnesium surface and, accelerating pitting and galvanic corrosion. It is desirable to minimize the degradation of magnesium during the coating process and therefore, a CaP bath (which contains no $Cl^-$ ion) can be employed to minimize the interference of corrosion during the formation of CaP coating layer. Further, a series of pre-coating treatments including thermal treatment passivation in alkaline solution to optimize the surface condition, can be employed. This multi-step approach can result in forming a crystal-like CaP coating on the magnesium alloy surface.

In accordance with certain embodiments of the invention and without intending to be bound by any particular theory, it is believed that deposition and formation of the peptide-containing coating on the magnesium alloy substrate can be effective to induce precipitation of CaP, which can result in the formation of a biomimetic CaP coating on the magnesium alloy. The peptide-induced coating can include an organized crystal pattern. That is, as compared to a CaP coating formed in the absence of biomimetic peptide, the peptide-induced coating can have an enhanced organized crystal pattern.

The peptide for use in the composition can be based on the highly acidic bone protein known as Dentin Sialophosphoprotein. Dentin Sialophosphoprotein (DSPP) is a non-collagenous ECM protein found in bone and teeth. Phosphophoryn (PP, also known as dentin phosphoprotein (DPP)) is a cleavage product of DSPP and has an important role in dentin mineralization, as well as cell signaling properties in bone and dentin. A member of the SIBLING family, PP can regulate various cellular activities such as the initiation of osteogenic gene expression via integrin/MAPK and Smad pathways. PP is an acidic Asp-Ser-rich protein containing 30% aspartic acid and 60% serine residues. It has a unique predominant sequence of Asp-Ser-Ser $(DSS)_n$ repeats with 85-90% of serines phosphorylated. This unique sequence contains high negatively charged amino acids which controls mineral formation in dentin. PP protein, however, has associated therewith rapid degradation and therefore, technical isolation of the PP protein can be challenging. Furthermore, the vast number of phosphorylated serine sites confer a high negative charge, making PP recalcitrant to further characterization and therefore, a biomimetic peptide approach is employed to overcome these challenges.

Generally, biomimetics is the study and development of synthetic systems that mimic the form, function, or structure of a biologically produced substance. Further, a biomimetic coating is a functional surface modification designed using biological concepts. Engineering of these coatings typically aims to improve compatibility of the surface with biological processes, such as cell signaling activity for enhanced cell proliferation and differentiation. In controlling magnesium corrosion, biomimetic coatings are of interest due to their potentially dual roles as coating materials: 1) affecting the kinetics of magnesium resorption, and 2) influencing cell signaling for better tissue regeneration. The biomimetic coating in combination with a resorbable metal can result in the metal degradation providing a release mechanism for the biological protein attached to the surface.

In accordance with principles of biomimicry, there is provided peptide motif based on the amino acid sequence of PP. This peptide is composed of three repeats of DSS amino acids. PP is an acidic Asp-Ser-rich protein containing 30% aspartic acid (Asp, D) and 60% Serine (Ser, S) residues.

In certain embodiments, a 3DSS biomimetic peptide is provided based on PP. The biomimetic 3DSS peptide can be coated onto the magnesium alloy to provide a biocompatible surface coating for improving corrosion resistance. The 3DSS peptide also can be used as a template for calcium phosphate deposition on the surface of the magnesium alloy. The 3DSS biomimetic peptide coating serves a protective role in both the hydrogen evolution and electrochemical corrosion.

In certain embodiments, the peptides for use in the invention include the following: (i) DEDE$(SSD)_n$DEG, wherein n represents the number of SSD motifs and is an integer from 2 to 20, indicated by SEQ NO. 1; (ii) RRRDEDE$(SSD)_n$DEG, wherein n represents the number of R-SSD motifs and is an integer from 2 to 20, indicated by SEQ NO. 2; (iii) RRRGDEDE$(SSD)_n$DEG, wherein n represents the number of SSD motifs and is an integer from 2 to 20, indicated by SEQ NO. 3; and (iv) LKKLKKLDEDE$(SSD)_n$DEG wherein n represents the number of SSD motifs and is an integer from 2 to 20, indicated by SEQ NO. 4.

Peptide (iii) above contains the RGD motif for cell integrin binding. Functional bioactive peptide motifs other than RGD can be used, such as but not limited to IKVAV of laminin. Thus, Peptide (iii) can also include RRRIKVAVE-DE$(SSD)_n$DEG. Peptide (iv) above contains leucine zipper domains to promote self-assembly.

The peptides for use in the coating compositions of the invention can induce biomimetic calcium phosphate mineralization of collagen fibrils. In the presence of these phosphorylated peptides, highly organized mineralized collagen fibrils structurally similar to the mineralized collagen fibrils of actual bone and dentin can be formed. Thus, DPP-inspired peptides can be used to synthesize highly organized biomimetic composite nanofibrils, with integrated organic and inorganic phases. These compositions are effective for use in the repair and regeneration of mineralized tissue, and the promotion of osteogenesis.

In certain embodiments, the bioinspired peptides include the following: (v) DEDESSDSSDSSDDEG (SSD3) indicated by SEQ NO. 1; (vi) RRRDEDESSDSSDSSDDEG (R-SSD3) indicated by SEQ NO. 2; (vii) RRRD-EDESSDSSDSSDSSDSSDDEG (R-SSDs) indicated by SEQ NO. 2; and (viii) RRRGDEDESSDSSDSSDDEG (RGD-SSD3) indicated by SEQ NO. 3.

In (viii) above indicated by SEQ NO. 3, the RGD motif provides for integrin binding for better integration into living tissues. These peptides can be phosphorylated at multiple sites. Further, these peptides can include other signaling self-assembly or molecular recognition motifs.

FIG. 1 shows a peptide design schematic of a R-SSD3 sequence containing: i) three Arg amino acids at its N-terminus end, ii) followed by four amino acids forming the CK1 recognition site and iii) three Ser-Ser-Asp repeats. CK2 recognition motif is located at the C-terminus end of the peptide. This peptide design schematic is in accordance with certain embodiments of the invention and is indicated by SEQ NO. 2. It has a unique predominant sequence of Asp-Ser-Ser (DSS)n repeats with 85-90% of serines phosphorylated. This unique sequence that contains high negatively charged amino acids can control mineral formation in dentin.

It is contemplated that other components may be added to the peptide-containing compositions provided that the biocompatibility and corrosion resistant properties of the coated article or substrate remain within acceptable limits.

In accordance with the invention, it is generally found that the combination of peptide and magnesium alloy, which includes the magnesium alloy being at least partially coated by the peptide-containing composition, provides cell signaling ability of full PP protein while being effective to promote osteogenesis and mineralization for improved tissue and bone regeneration. Further, as previously mentioned herein, the peptide-containing coating may control CaP deposition to achieve a biomimetic CaP coating. Such a coating has high compatibility in a mineralizing tissue site, and thereby can further improve the cellular compatibility of alloy implants.

Further, it is contemplated that a pre-treatment, e.g., conversion coating may be conducted or applied to the surface of the metal alloy prior to applying thereto, or depositing thereon, the peptide-containing coating composition. In certain instances, it has been shown in the art that pre-treatment can result in improved adhesion of a coating to a substrate.

Moreover, in accordance with certain embodiments of the invention, it has been shown that coating of peptides can be achieved on magnesium based alloys and as a result, corrosion resistant properties are provided to the magnesium based alloys. Without intending to be bound by any particular theory, it is believed that the resorbable magnesium alloy acts as a protein/peptide delivery system.

EXAMPLES

The examples demonstrate the effectiveness of coating biomimetic peptides on magnesium (Mg) alloy AZ31B (96% magnesium, 3% aluminum, 1% zinc) and includes, examining the consequent reduction in corrosion rate in simulated body fluids (SBF), and assessing the ability of the biomimetic peptide to induce calcium phosphate precipitation on AZ31B alloys. The commercially-available (AZ31B) alloy was selected as a prototype substrate because it is a major, low-cost commercial Mg alloy and AZ31 implants were believed to have potential in facilitating new bone formation.

Mg Alloy Preparation

An AZ31B alloy (1 mm thick, Alfa Aesar) was used as the primary substrate material. Samples were cut to 10×10 mm$^2$ squares, and then polished on both sides using 800 grit silicon carbide (SiC, Allied) papers to obtain homogeneous roughness. The final dimension of the finished substrate was 10×10×1 mm$^3$. Before experimentation, all samples were ultrasonically cleaned in 100% acetone for 10 minutes, then in 100% ethanol for 10 minutes, in order to remove any surface residues. All samples received a final rinse in deionized water (DI water). Clean AZ31B alloys were placed under ultraviolet radiation for one hour on each side for sterilization. Sterilized AZ31B alloys were then used as non-coated controls. In order to stabilize the surface prior to coating, all AZ31B samples used to perform the CaP-coating received the following pre-treatments: (i) heat treatment at 205° C. for one hour in argon; (ii) passivation in 1M NaOH for 24 hours; and (iii) heat treatment at 150° C. for one hour in air.

Biomimetic Peptide Coating

A biomimetic ECM peptide motif was designed based on the sequence of PP protein. This novel peptide comprises a triple repeat of a tri-residue sequence [aspartic acid—serine—serine]RRRDEDE(SSD)$_3$DEG, indicated by SEQ NO. 2. This designed peptide sequence was sent to 21$^{st}$ Century Biochemicals, Inc., for synthesis.

The 3DSS peptide powder was dissolved in tetrahydrofuran (THF, Fisher Scientific) at a final concentration of 606 g/mL. The peptide was coated onto AZ31B alloys by immersion of the AZ31B samples in the peptide-THF solution at room temperature (RT) for two days, until the THF evaporated completely. AZ31B samples were then further dried in air for two more days. THF-coated AZ31B controls were prepared with the same method, however with no 3DSS peptide dissolved in THF. The coating process is schematically described in FIG. 2B.

Calcium Phosphate Coating

CaP solution was prepared as calcium and phosphate precursor solutions separately, then mixed to form a final CaP bath. The final concentration (mM) of the CaP bath was 14 mM of Ca(NO$_3$)$_2$, 8.4 mM of NaH$_2$PO$_4$ and 4 mM NaHCO$_3$. The achieved Ca/P ratio was 1.67, which is close to that of hydroxyapatite (HA). Sodium bicarbonate (NaHCO$_3$) was added to the phosphate solution as a buffering element.

Figure 2A:
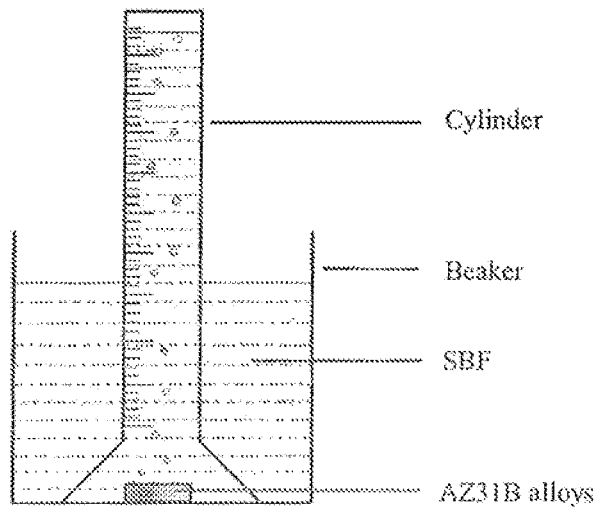
FIG. 2A is a schematic showing the apparatus set-up for measuring hydrogen evolution, for use in certain embodiments of the invention.
Figure 2B:
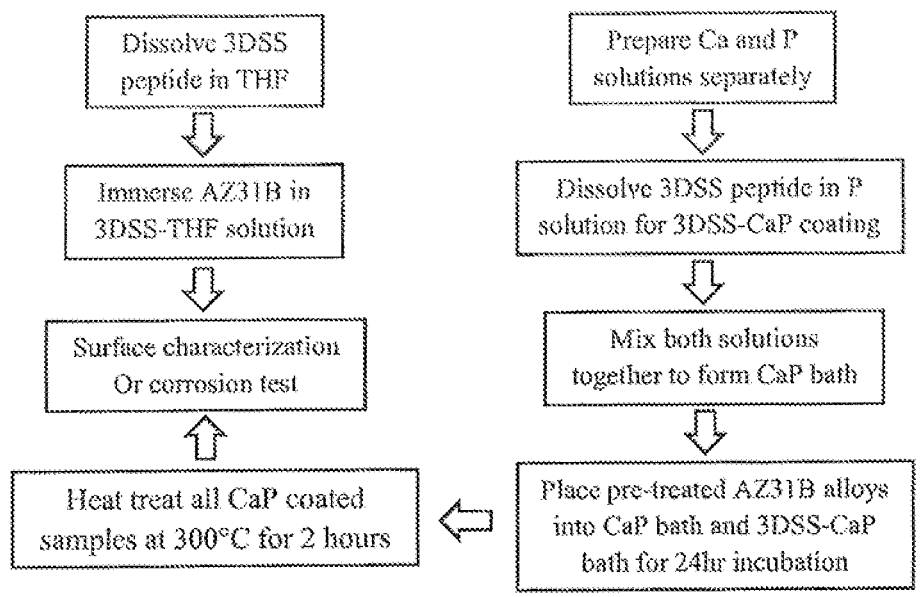
FIG. 2B is a schematic flow diagram showing coating processes for use in certain embodiments of the invention.

3DSS biomimetic peptides were added to the phosphate solution during the preparation. The final concentration of the biomimetic 3DSS peptides in the CaP bath was 125 µg/mL. A CaP bath containing no peptide was used for the control group. Pre-treated AZ31B alloys were placed in the CaP bath and incubated for 24 hours at RT. After CaP coating, all samples were rinsed in DI water, and then followed with a final heat treatment at 300° C. for two hours (FIG. 2B).

Surface Characterization

Scanning electron microscopy (SEM, JSM-6330F, JEOL) was conducted on all peptide-coated samples and CaP coated samples to assess coating morphology, distribution and structure. Elemental composition of the 3DSS coating and CaP coating were analyzed using energy dispersive X-ray spectroscopy (EDX) coupled with SEM (Phillips, XL-30 FEG SEM). An EDX detector was attached to the SEM system, and employed a beryllium-window protected Si (Li) detector operating at 15 kV for elemental analysis. Non-coated AZ31B and THF-coated AZ31B alloys were used as controls for 3DSS biomimetic peptide coating, and CaP-coated AZ31B alloys were used as controls for 3DSS biomimetic peptide induced CaP coating experiments.

Diffuse-reflectance infrared spectroscopy (DRIFT, Nexus 470 FTIR, Thermo Electron Corp) was used to characterize the chemical composites of coatings. All spectra were collected in the range of 4000-400 cm$^{-1}$ for 1024 scans with a resolution at 4 cm$^{-1}$. Bare AZ31B alloys were used as background for all experiments. Pure 3DSS peptide powder was used as a positive control for 3DSS biomimetic peptide coating experiments. CaP coated AZ31B alloys were used as controls for 3DSS biomimetic peptide induced CaP coating. Both CaP coatings received a final 300° C. heat treatment.

Corrosion Assessment

The corrosion resistance of 3DSS peptide-coated AZ31B alloys was assessed using two techniques. The first technique, hydrogen (H$_2$) evolution testing in SBF, was carried out at RT, using non-coated AZ31B alloys as controls. SBF solution was prepared. Ion concentrations (mM) were as follows: 142.0 of Na$^+$, 5.0 of K$^+$, 1.5 of Mg$^{2+}$, 2.5 of Ca$^{2+}$, 148.8 of Cl$^-$, 4.2 of HCO$_3^-$, 1.0 of HPO$_4^{2-}$ and 0.5 of SO$_4^{2-}$. Each AZ31B sample was immersed in SBF for 72 hours. The schematic diagram of the experimental setup is shown in FIG. 2A. The amount of corroded Mg was calculated according to the corrosion reaction expressed as follows: Mg+2H$_2$O=Mg$^{2+}$+2OH+H$_2$ (Equation 1). A t-test was used to evaluate the difference in corrosion rate. Statistical significance was defined as $p<0.05$.

The second technique, electrical corrosion assessment, was also applied to monitor the corrosion behavior of 3DSS peptide-coated AZ31B alloys. Electrochemical corrosion study was carried out in Dulbecco's Modified Eagle Medium (DMEM, Gibco), which was supplemented with 10% fetal bovine serum (FBS, Gibco), 1% glutamine, 1% penicillin and streptomycin to meet the physiological conditions for cell culture. An electrochemical workstation (CH instruments, Inc. 604A) with a three electrode cell configuration was used. The temperature was maintained at 37° C. Platinum was used as the counter electrode while Ag/AgCl was used as the reference electrode. The potentiodynamic polarization (PDP) curve was recoded with a scanning rate of ~1 mV/s. The potential window was set from −2.0V to −1.0V. Bare AZ31B alloys as well as 3DSS peptide-coated AZ31B alloys were used as a working electrode with one surface connected to an electrical wire, the other surface exposed to the media (surface area was 1 cm$^2$). The corrosion potential and the corrosion current density were determined by linear fit of the Tafel plots.

Results

AZ31B Mg Alloys Coated with Biomimetic Peptides

SEM results showed that a smooth, compact coating formed evenly on AZ31B alloy treated with 3DSS peptide. In contrast, on the non-coated AZ31B alloy and the THF-coated AZ31B alloy, polishing marks were clearly evident. These results indicated the ability to successfully create a coating layer on AZ31B alloys. To demonstrate that this coating layer was indeed composed of peptide, EDX and DRIFT analyses were performed for further coating characterization.

The atomic composition of the surface coating was analyzed via SEM associated with EDX. EDX analysis revealed the presence of Mg and O atoms on both non-coated AZ31B and THF-coated AZ31B. The presence of O atom was due to oxidization on the surface of AZ31B alloys. In addition to Mg and O atoms, C and N atoms were also presented on the surface of 3DSS peptide-coated AZ31B alloy. These atoms were mainly from the carbon backbone and amine bonds in the peptide. The number of Mg atoms also decreased dramatically due to peptide coverage on the Mg alloy surface. These results confirmed that the coating layer created on AZ31B surface was indeed 3DSS peptide. The atoms presented on the alloy surface in weight (wt) % for the non-coated AZ31B were: 19.46 of O and 80.54 of Mg; for the THF-coated AZ31B were: 5.37 of O and 94.63 of Mg; and for the 3DSS coated AZ31B were: 64.80 of C 8.96 of N, 14.82 of O and 10.29 of Mg. The atoms presented on the alloy surface in atomic (At) % for the non-coated AZ31B were: 26.86 of O and 73.14 of Mg; for the THF-coated AZ31B were: 7.93 of O and 92.07 of Mg; and for the 3DSS coated AZ31B were: 72.65 of C 8.62 of N, 12.47 of O and 5.70 of Mg. To further support these results, DRIFT assessment was applied to characterize the chemical composites of the coatings.

In the DRIFT spectrum of pure 3DSS peptide powder, a peak at 3300 cm$^{-1}$ corresponded to an amide A band and was indicative of a terminal amine group due to the N—H stretching vibration in the peptide. Peaks at 1660 cm$^{-1}$ and 1550 cm$^{-1}$ corresponded to an amide I band (mainly associated with the C=O stretching vibration) and an amide II band (resulting from the N—H bending vibration and from the C—N stretching vibration), respectively. After deposition of the peptide on AZ31B, the DRIFT spectrum also contained the amide A band (3300 cm$^{-1}$), amide I band (1670 cm$^{-1}$) and amide II band (1540 cm$^{-1}$), with a similar pattern in the spectrum of peptide powder. The spectrum was slightly shifted due to the fact that the peptide was presented on the Mg alloy surface. This result confirmed that the coating presented on AZ31B alloys was peptide.

3DSS Peptide Coating Significantly Improved Mg Alloy Corrosion Resistance

Results were obtained for hydrogen evolution tests of AZ31B alloys in SBF solution. The accumulated H$_2$ volumes of AZ31B alloys exhibited an approximately linear relationship with immersion time. H$_2$ released from 3DSS coated AZ31B alloys was consistently less than that released from non-coated AZ31B alloys. For example, at starting time point (~0.5 hours), H$_2$ released from non-coated AZ31B samples was 1.33 times more than that released from 3DSS-coated AZ31B. After immersion for 72 hours, non-coated AZ31B still generated 1.30 times more H$_2$ than 3DSS-coated AZ31B. The t-test showed that the difference in amount of released H$_2$ between 3DSS-coated AZ31B and non-coated AZ31B after immersion in SBF for 3 hours, was significant ($p<0.05$).

According to the corrosion reaction (Equation 1), 1 mol of H$_2$ gas corresponds to the corroding of 1 mol of Mg. The total amount of corroded Mg detected was 9.7 mg for a non-coated AZ31B alloy and 7.5 mg for the 3DSS coated the AZ31B alloy. (This assumed that the alloying elements aluminum (3%) and zinc (1%) in AZ31B alloy were few, and their reaction in SBF was negligible.) The corrosion results demonstrated that the 3DSS peptide coating significantly improved the corrosion resistance of AZ31B alloys in SBF.

The average H$_2$ evolution rate of AZ31B alloys was calculated based on the surface area of AZ31B alloys (10×10×1 mm$^3$ with a total surface area of 2.4 cm$^2$), the total volume of released H$_2$, (9.03 mL for non-coated AZ31B and 6.93 mL for 3DSS peptide coated AZ31B) and the immersion time (72 hrs). The average H$_2$ evolution rate of non-coated AZ31B alloy was 1.254 mL/cm$^2$·day$^{-1}$. The average H$_2$ evolution rate of 3DSS peptide-coated AZ31B was 0.96 mL/cm$^2$·day$^{-1}$. These average H$_2$ evolution rates can be used as indicators of AZ31B corrosion rates. Thus, the numbers represent a 30% overall reduction over corrosion of non-coated AZ31B.

The corrosion rate was also estimated by calculating the slopes of the linear region of the two curves, which were 0.1 for non-coated AZ31B and 0.075 for 3DSS peptide-coated AZ31B, respectively. A larger slope indicated a higher corrosion rate.

PDP curves (Tafel plot) of bare AZ31B alloy and 3DSS peptide-coated AZ31B alloy in DMEM media were generated. The anodic reaction was the dissolution of Mg by oxidation, whereas the cathodic reaction was the H$_2$ evolution through a reduction process. The corrosion potential for non-coated AZ31B control and 3DSS-peptide coated AZ31B were −1.50 V and −1.14 V, respectively. The corrosion potential of 3DSS peptide-coated AZ31B was ~400 mV higher as compared to non-coated AZ31B control. The 3DSS peptide-coated AZ31B also exhibited a much lower corrosion current: for 3DSS peptide-coated AZ31B, the Ico-3DSS was 3.16e$^{-4}$ µA; for non-coated AZ31B control, the I$_{corr}$ was 3.16 µA (given the exposed surface area 1 cm$^2$). These results indicated that coated AZ31B was more stable (corrosion-resistant) in DMEM, due to the protective properties of the 3DSS biomimetic peptide coatings.

Biomimetic Peptides Facilitated Organized Calcium Phosphate Precipitation

To further extend the efficacy of Mg alloy coating, it was tested whether peptide undercoating could control the deposition of CaP on the alloy surface.

SEM results of CaP coating and 3DSS peptide-induced CaP coating on AZ31B alloys were obtained. The crystal structures and morphologies of CaP coatings on the AZ31B surface with and without 3DSS were compared. The CaP coating formed in the presence of 3DSS peptide clearly exhibited a larger, crystal-like structure as compared to that of the CaP coating formed without the facilitation of 3DSS peptide. These results showed the ability to precipitate CaP coatings onto AZ31B alloys, and a distinct difference in the CaP crystal structures with and without the presence of 3DSS biomimetic peptide. This data clearly indicated that the bioinspired 3DSS peptide was inducing CaP precipitation in an organized crystal pattern.

EDX and DRIFT analysis were also performed to further characterize the chemical structures of the CaP coatings.

The atomic composition of the newly formed CaP coating, analyzed by SEM with associated EDX was generated.

EDX analysis revealed the presence of C, O, Mg, P, and Ca atoms on both CaP-coated AZ31B alloys with and without 3DSS peptide. There was also a negligible peak of Al atom (0.38%, wt %) on the surface of 3DSS-induced CaP coated AZ31B. The O, P and Ca atoms were from the CaP coatings on the surface of AZ31B alloys. In addition to O, P, and Ca atoms, atom C was also presented on both CaP coated AZ31B, which mainly derived from the sodium bicarbonate ($NaHCO_3$) in the CaP bath. The amount of each atom in different CaP coatings was very similar. The Ca/P ratio in each CaP-coated sample, before and after final 300° C. heat treatment, was calculated based on the EDX data. The atoms presented on the alloy surface in weight (wt) % for the 3DSS induced CaP coated AZ31B were: 11.15 of C, 31.56 of O, 4.05 of Mg, 0.38 of Al, 20.18 of P and 32.68 of Ca; and for the CaP coated AZ31B without 3DDS were: 8.02 of C, 27.36 of O, 2.69 of Mg, 21.54 of P and 40.39 of Ca. The atoms presented on the alloy surface in atomic (At) % for the 3DSS induced CaP coated AZ31B were: 20.40 of C, 43.37 of O, 3.66 of Mg, 0.31 of Al, 14.32 of P and 17.92 of Ca; and for the CaP coated AZ31B without 3DDS were: 15.93 of C, 40.08 of O, 2.64 of Mg, 16.59 of P and 24.04 of Ca. The Ca/P ratio of both CaP coatings was around 1.3. In particular, the Ca/P ratios characterized by EDX for the 3DSS-induced CaP coated AZ31B before 300° C. heat treatment was 1.38+/−0.16 and after 300° C. heat treatment was 1.31+/−0.03 and, the Ca/P ratios characterized by EDX for the CaP coated AZ31B without 3DSS before 300° C. heat treatment was 1.34+/−0.10 and after 300° C. heat treatment was 1.30+/−0.09. This lower Ca/P ratio (lower than 1.67) may have been due to the incorporation of carbonate in HA structure.

DRIFT assessment was applied to characterize the chemical composites of CaP coatings. Both CaP coatings received a final 300° C. heat treatment. For the DRIFT spectra of both CaP coatings on AZ31B with and without the presence of 3DSS peptide, hydroxyl (OH) stretch was observed at 3544 $cm^{-1}$ in the spectrum of CaP coated AZ31B, and at 3550 $cm^{-1}$ in the 3DSS peptide-induced CaP-coated AZ31B. However, the intensity of each peak was very low, and both peaks were masked by the broad $H_2O$ peak. Both spectra exhibited typical peaks of the v1, v3 phosphate ($PO_4^{3-}$) region (900-1200 $cm^{-1}$) of HA. Both contours presented one sharp peak at around 1010 $cm^{-1}$, and a shoulder peak around 1116 $cm^{-1}$. The split of $PO_4^{3-}$ v1, v3 peaks indicated that the phase of CaP coating formed on the AZ31B surface was HA. Whereas amorphous calcium phosphate typically exhibits a single band. There was also a well-defined doublet at around 600 $cm^{-1}$ (one peak at 600 $cm^{-1}$, another peak at 560 $cm^{-1}$) in each spectrum, corresponding to $PO_4^{3-}$ v4 bending frequency. The peaks presented around 1300-1650 $cm^{-1}$ in both spectra (one peak at around 1600 $cm^{-1}$, another peak at around 1400 $cm^{-1}$) resulted from carbonate ($CO_3^{2-}$) v3 vibration. These data indicated that the CaP coating was a mixture of HA and carbonated apatite, since there was $NaHCO_3$ in the CaP bath. To verify the DRIFT results, x-ray diffraction measurements were performed to confirm that the CaP formed was HA.

Discussion of Results

The surface modifications developed for Mg-based alloys using various coating materials have led to variable results in enhancing corrosion resistance. It is contemplated that a suitable coating on Mg alloy implants has at least one of the following properties: adheres strongly on the surface, as well as being environmentally friendly, is degradable, and is biocompatible with the human body.

Coating Methods

A non-aqueous environment was employed for the Mg alloy substrates using an organic solution (e.g., THF) as a solvent for the biomimetic peptide coating. This method provided an advantage of conserving the surface integrity while forming a homogeneous coating on the magnesium without concomitant corrosion reaction.

Corrosion Test

As previously mentioned herein, $H_2$ gas released from a corroding Mg alloy implant is a significant concern for medical application of Mg, since this gas can accumulate in the body, form $H_2$ gas pockets and cause the separation of tissue layers, as well as other negative biological consequences. Because it provides precise and direct information on the amount of $H_2$ gas generated, $H_2$ evolution measurement is increasingly used as a measure of the corrosive behavior of Mg alloy. According to Equation 1 (above), measuring the gas volume can yield a value for the mass loss of Mg, a value that is not affected by the formation of corrosion products. Unfortunately, $H_2$ evolution does not provide any information on the actual mechanisms of corrosion. For this reason, a PDP test was included, which provided additional details of the mechanistic aspects of Mg alloy corrosion. By combining two techniques and using two different corrosion solutions (SBF and DMEM media), the peptide coating's protective effect on alloy corrosion was assessed by comparing the coated vs. non-coated samples. The data showed that the 3DSS peptide coating was effective in reducing the rate of Mg corrosion. However, it was noted that corrosion behavior can vary greatly due to variations with conditions, such as the use of differing Mg alloys and/or immersion solutions.

Calcium Phosphate Coatings

A CaP bath (which contained no $Cl^-$ ion) was employed to minimize the interference of corrosion during the formation of CaP coating layer. In some instances, CaP layers led to initially good cell adhesion and spreading, but had compromised viability at longer time points. This was likely due to the poor corrosion protection properties of a CaP layer alone. Thus, a biomimetic peptide was used to direct the precipitation of CaP on Mg alloy. The biomimetic peptide, by mimicking the bioactivity of full PP protein, had the ability to induce controlled CaP precipitation, resulting in a biologically advantageous CaP microstructure. It was believed that these peptide-induced CaP coatings would result in a more homogeneous coating and more would provide better corrosion resistance. A series of pre-coating treatments were tested for the purpose of providing an enhanced and more stable Mg alloy surface for receiving the CaP coatings. For example, NaOH passivation to reduce the initial corrosion in a CaP bath, and strongly enhancing the likelihood for subsequent cell survival on the coated surface was employed. Alternatively, after heat treatment the CaP coating can form more easily on the substrate, potentially overcoming the energy barrier of apatite crystal nucleation and resulting in evenly distributed grains of crystallization.

From the SEM results, there was observed distinct differences in crystal morphology for 3DSS peptide-induced CaP coatings, as compared to the CaP coatings without 3DSS. Larger crystals formed by the organizational effect of 3DSS peptide indicated crystals with higher order fidelity, and also indicated more uniformity of the phosphate ions.

The Ca/P ratio was calculated based on the EDX results. There was observed a slight decrease in Ca/P ratio after the CaP coated samples being treated at 300° C. The Ca/P ratio of both CaP coatings was around 1.3, both before and after the heat treatment. This lower Ca/P ratio (lower than 1.67)

may have indicated a mixture of different CaP phases, which may have been due to the incorporation of carbonate in HA structure.

In addition, DRIFT results confirmed a mixed composition of crystalline HA and carbonated apatite. There was observed a very low intensity of OH peak in both CaP coatings with and without 3DSS peptide. This decrease in OH groups may have been attributed to the existence of carbonate in the CaP bath. That is, the OH group decreased with an increase in the carbonated substitution. The presence of $CO_3^{2-}$ in the CaP coatings may have been from either surface deposits of carbonate or the $CO_3^{2-}$ was incorporated in CaP structure. The two peaks at 900-1200 cm$^{-1}$ were not sharply defined and were poorly split, indicating that the HA coatings were poorly crystallized. The sharp splitting of the P—O band around 600 cm$^{-1}$ ($PO_4^{3-}$ v4) indicated a crystalline apatite structure (HA), since a completely amorphous CaP should have only one single broad peak at this region. The distribution of $CO_3^{2-}$ v3 sites depended on the maturation and formation of apatite crystals. The competition between $PO_4^{3-}$ and $CO_3^{2-}$ affected the occupancy of $CO_3^{2-}$ v3 sites. The presence of $CO_3^{2-}$ v3 may have contributed to the decrease of OH groups in the spectra as mentioned previously. The two spectra were very similar in shape, and the atomic analysis by EDX also showed very similar types and amounts of atoms derived from CaP coatings with and without 3DSS peptide.

CONCLUSION

There was demonstrated the formation of a biomimetic peptide coating on AZ31B alloy. Surface characterizations by SEM-EDX and DRIFT results confirmed the presence of biomimetic peptides on the surface of AZ31B alloys. Two different corrosion tests revealed an increased corrosion resistance for peptide-coated AZ31B alloys. It also was demonstrated that biomimetic 3DSS peptide can direct CaP formation on the AZ31B alloys and result in very different CaP crystal structure as compared to CaP coatings without the presence of 3DSS peptide. EDX and DRIFT indicated the composition of crystalline HA and carbonated apatite.

The results demonstrated the effectiveness of applying biomimetic coatings to magnesium-based alloys for corrosion protection. It also was demonstrated that 3DSS biomimetic peptide coatings can organize CaP precipitation. Thus, biomimetic peptide-coated magnesium alloy substrates are suitable for use as medical implants for improved osteointegration.

Whereas particular embodiments of the invention have been described herein for purposes of illustration, it will be evident to those skilled in the art that numerous variations of the details may be made without departing from the invention as set forth in the appended claims.

The invention claimed is:

1. A composition for coating magnesium alloy, comprising:
a peptide, which comprises:
RRRDEDE(SSD)$_n$DEG, wherein n is an integer selected from 3 and 5, indicated by SEQ NO. 2.

2. The composition of claim 1, wherein the peptide comprises:
RRRDEDESSDSSDSSDDEG, indicated by SEQ NO. 2.

3. A coated magnesium alloy substrate, comprising:
a coating composition, which comprises:
a peptide comprising:
RRRDEDE(SSD)$_n$DEG, wherein n is an integer selected from 3 and 5, indicated by SEQ NO. 2.

4. The coated magnesium alloy substrate of claim 3, wherein the peptide comprises:
RRRDEDESSDSSDSSDDEG, indicated by SEQ NO. 2.

5. A method of preparing a biomimetic magnesium alloy medical device, the method comprising:
making a coating composition comprising a peptide, which comprises:
RRRDEDE(SSD)$_n$DEG, wherein n is an integer selected from 3 and 5, indicated by SEQ NO. 2;
depositing the coating composition on a least a portion of an outer surface of an uncoated magnesium alloy medical device to form a coating thereon; and
producing a coated magnesium alloy medical device.

6. The method of claim 5, further comprising implanting the coated magnesium alloy medical device into the body of a patient.

7. The method of claim 5, wherein the forming and the depositing of the coating composition, comprises:
obtaining a peptide in the form of a powder, which comprises:
RRRDEDE(SSD)$_n$DEG, wherein n is an integer selected from 3 and 5, indicated by SEQ NO. 2;
dissolving the peptide in an organic solvent to form a peptide solution;
combining the peptide solution with calcium phosphate solution to form a peptide/calcium phosphate bath solution;
immersing the uncoated magnesium alloy medical device into the peptide/calcium phosphate bath solution to form the coating on the surface of the magnesium medical device.

8. The method of claim 7, wherein the organic solvent is tetrahydrofuran.

* * * * *

SEQUENCE LISTING

```
<160> NUMBER OF SEQ ID NOS: 4

<210> SEQ ID NO 1
<211> LENGTH: 67
<212> TYPE: PRT
<213> ORGANISM: Artificial
<220> FEATURE:
<223> OTHER INFORMATION: derived from consensus mammalian sequence of
      DSPP
<220> FEATURE:
<221> NAME/KEY: MISC_FEATURE
<222> LOCATION: (5)..(64)
<223> OTHER INFORMATION: [Ser Ser Asp] repeats (n varies from 2 to 20)
<220> FEATURE:
<221> NAME/KEY: MISC_FEATURE
<222> LOCATION: (1)..(4)
<223> OTHER INFORMATION: Casein kinase 1 recognition motif
<220> FEATURE:
<221> NAME/KEY: MISC_FEATURE
<222> LOCATION: (65)..(67)
<223> OTHER INFORMATION: Casein kinase 2 recognition motif

<400> SEQUENCE: 1

Asp Glu Asp Glu Ser Ser Asp Ser Ser Asp Ser Ser Asp Ser Ser Asp
1               5                   10                  15

Ser Ser Asp Ser Ser Asp Ser Ser Asp Ser Ser Asp Ser Ser Asp Ser
                20                  25                  30

Ser Asp Ser Ser Asp Ser Ser Asp Ser Ser Asp Ser Ser Asp Ser Ser
            35                  40                  45

Asp Ser Ser Asp Ser Ser Asp Ser Ser Asp Ser Ser Asp Ser Ser Asp
        50                  55                  60

Asp Glu Gly
65

<210> SEQ ID NO 2
<211> LENGTH: 70
<212> TYPE: PRT
```

<213> ORGANISM: Artificial
<220> FEATURE:
<223> OTHER INFORMATION: derived from consensus mammalian sequence of
      DSPP
<220> FEATURE:
<221> NAME/KEY: MISC_FEATURE
<222> LOCATION: (8)..(68)
<223> OTHER INFORMATION: [Asp Ser Ser] repeats (n varies from 2 to 20)
<220> FEATURE:
<221> NAME/KEY: MISC_FEATURE
<222> LOCATION: (1)..(3)
<223> OTHER INFORMATION: Insertion of 3 Arg at the N terminus of the
      peptide
<220> FEATURE:
<221> NAME/KEY: MISC_FEATURE
<222> LOCATION: (4)..(7)
<223> OTHER INFORMATION: Casein kinase 1 recognition motif
<220> FEATURE:
<221> NAME/KEY: MISC_FEATURE
<222> LOCATION: (69)..(71)
<223> OTHER INFORMATION: Casein kinase 2 recognition motif

<400> SEQUENCE: 2

Arg Arg Arg Asp Glu Asp Glu Ser Ser Asp Ser Ser Asp Ser Ser Asp
1               5                   10                  15

Ser Ser Asp Ser Ser Asp Ser Ser Asp Ser Ser Asp Ser Ser Asp Ser
                20                  25                  30

Ser Asp Ser Ser Asp Ser Ser Asp Ser Ser Asp Ser Ser Asp Ser Ser
            35                  40                  45

Asp Ser Ser Asp Ser Ser Asp Ser Ser Asp Ser Ser Asp Ser Ser Asp
        50                  55                  60

Ser Ser Asp Asp Glu Gly
65                  70

<210> SEQ ID NO 3
<211> LENGTH: 71
<212> TYPE: PRT
<213> ORGANISM: Artificial
<220> FEATURE:
<223> OTHER INFORMATION: derived from consensus mammalian sequence of
      DSPP
<220> FEATURE:
<221> NAME/KEY: MISC_FEATURE
<222> LOCATION: (9)..(69)
<223> OTHER INFORMATION: [Asp Ser Ser] repeats (n varies from 2 to 20)
<220> FEATURE:
<221> NAME/KEY: MISC_FEATURE
<222> LOCATION: (1)..(3)
<223> OTHER INFORMATION: Insertion of 3 Arg at the N terminus of the
      peptide
<220> FEATURE:
<221> NAME/KEY: MISC_FEATURE
<222> LOCATION: (4)..(4)
<223> OTHER INFORMATION: Insertion of Gly to generate an Arg Gly Asp
      integrin recognition motif. Other signalling motifs, such as IKVAV
      can be inserted into the sequence
<220> FEATURE:
<221> NAME/KEY: MISC_FEATURE
<222> LOCATION: (5)..(8)
<223> OTHER INFORMATION: Casein kinase 1 recognition motif
<220> FEATURE:
<221> NAME/KEY: MISC_FEATURE
<222> LOCATION: (70)..(73)
<223> OTHER INFORMATION: Casein kinase 2 recognition motif

<400> SEQUENCE: 3

Arg Arg Arg Gly Asp Glu Asp Glu Ser Ser Asp Ser Ser Asp Ser Ser
1               5                   10                  15

Asp Ser Asp Ser Ser Asp Ser Ser Asp Ser Ser Asp Ser Ser Asp
                20                  25                  30

```
Ser Ser Asp Ser Ser Asp Ser Ser Asp Ser Ser Asp Ser Asp Ser
        35                  40                  45

Ser Asp Ser Ser Asp Ser Ser Asp Ser Ser Asp Ser Ser Asp Ser
    50                  55                  60

Asp Ser Ser Asp Asp Glu Gly
65                  70

<210> SEQ ID NO 4
<211> LENGTH: 74
<212> TYPE: PRT
<213> ORGANISM: Artificial
<220> FEATURE:
<223> OTHER INFORMATION: derived from consensus mammalian sequence of
      DSPP
<220> FEATURE:
<221> NAME/KEY: MISC_FEATURE
<222> LOCATION: (12)..(72)
<223> OTHER INFORMATION: [Asp Ser Ser] repeats (n varies from 2 to 20)
<220> FEATURE:
<221> NAME/KEY: MISC_FEATURE
<222> LOCATION: (8)..(11)
<223> OTHER INFORMATION: Casein kinase 1 recognition motif
<220> FEATURE:
<221> NAME/KEY: MISC_FEATURE
<222> LOCATION: (73)..(75)
<223> OTHER INFORMATION: Casein kinase 2 recognition motif
<220> FEATURE:
<221> NAME/KEY: MISC_FEATURE
<222> LOCATION: (1)..(7)
<223> OTHER INFORMATION: Leucine zipper motif

<400> SEQUENCE: 4

Leu Lys Lys Leu Lys Lys Leu Asp Glu Asp Glu Ser Ser Asp Ser Ser
1               5                   10                  15

Asp Ser Ser Asp Ser Ser Asp Ser Ser Asp Ser Ser Asp Ser Ser Asp
            20                  25                  30

Ser Ser Asp Ser Ser Asp Ser Ser Asp Ser Ser Asp Ser Ser Asp Ser
        35                  40                  45

Ser Asp Ser Ser Asp Ser Ser Asp Ser Ser Asp Ser Ser Asp Ser Ser
    50                  55                  60

Asp Ser Ser Asp Ser Ser Asp Asp Glu Gly
65                  70
```